(12) United States Patent
Kurtz et al.

(10) Patent No.: US 10,327,664 B2
(45) Date of Patent: Jun. 25, 2019

(54) SYSTEM, METHOD AND APPARATUS FOR DETECTING AN EVOKED RESPONSE SIGNAL

(71) Applicants: VIVOSONIC INC., Etobicoke (CA); Debbie Kurtz, Toronto (CA)

(72) Inventors: Isaac Kurtz, Toronto (CA); Aaron Steinman, Toronto (CA); Stephen Allan Rowlands, Etobicoke (CA)

(73) Assignee: VIVOSONIC INC., Etobicoke, Ontario (CA)

( * ) Notice: Subject to any disclaimer, the term of this patent is extended or adjusted under 35 U.S.C. 154(b) by 140 days.

(21) Appl. No.: 15/513,196

(22) PCT Filed: Sep. 24, 2015

(86) PCT No.: PCT/CA2015/050950
§ 371 (c)(1),
(2) Date: Mar. 22, 2017

(87) PCT Pub. No.: WO2016/044942
PCT Pub. Date: Mar. 31, 2016

(65) Prior Publication Data
US 2017/0245776 A1 Aug. 31, 2017

Related U.S. Application Data

(60) Provisional application No. 62/054,538, filed on Sep. 24, 2014.

(51) Int. Cl.
*A61B 5/00* (2006.01)
*A61B 5/0484* (2006.01)
*A61B 5/12* (2006.01)

(52) U.S. Cl.
CPC ........ *A61B 5/0484* (2013.01); *A61B 5/04842* (2013.01); *A61B 5/04845* (2013.01);
(Continued)

(58) Field of Classification Search
CPC ... G06F 17/10; A61B 5/04842; A61B 5/0484; A61B 5/04845; A61B 5/125; A61B 5/4821; A61B 5/7203
See application file for complete search history.

(56) References Cited

U.S. PATENT DOCUMENTS

| | | | |
|---|---|---|---|
| 7,976,473 B2* | 7/2011 | Causevic | A61B 5/04845 600/558 |
| 2003/0073920 A1* | 4/2003 | Smits | A61B 5/04845 600/544 |

FOREIGN PATENT DOCUMENTS

| | | |
|---|---|---|
| EP | 1578490 A1 | 9/2005 |
| WO | 2005072459 A2 | 8/2005 |
| WO | 2006122349 A1 | 11/2006 |

OTHER PUBLICATIONS

Sokolov, Y., "Auditory Evoked Potentials: Signals, Noises, & Clear Recording Through New Technologies—In-Situ Amplification, Wireless Communications, & Kalman Filtering", NCHAM Workshop, Apr. 21-22, 2005, Albuquerque, NM, United States of America.

(Continued)

*Primary Examiner* — Bryan Bui
(74) *Attorney, Agent, or Firm* — Marks & Clerk

(57) ABSTRACT

A method for detection of an evoked response signal in noise including: generating a plurality of stimuli; receiving a noisy signal related to an evoked response to the plurality of stimuli; divide the noisy signal into a plurality of responses to the plurality of stimuli; estimate a statistic matrix for the plurality of responses; shrink the statistic matrix; calculate weights based on an inverse of the shrunk statistic matrix; apply weights to the plurality of responses to construct a final response; and output the final response. An apparatus having an input device configured to receive data related to a plurality of stimuli; and a processor configured to: receive a noisy signal and divide the noisy signal into a plurality of (Continued)

responses; estimate a statistic matrix; shrink the statistic matrix; calculate weights based on an inverse of the shrunk statistic matrix; and apply weights to the plurality of responses to construct a final response.

26 Claims, 11 Drawing Sheets

(52) U.S. Cl.
CPC ............ *A61B 5/125* (2013.01); *A61B 5/4821* (2013.01); *A61B 5/7203* (2013.01)

(56) References Cited

OTHER PUBLICATIONS

Canadian Intellectual Property Office as International Searching Authority, International Search Report and Written Opinion on PCT Appln. No. PCT/CA2015/050950, dated Dec. 3, 2015.

* cited by examiner

SYSTEM, METHOD AND APPARATUS FOR DETECTING AN EVOKED RESPONSE SIGNAL

RELATED APPLICATIONS

The present disclosure claims priority to U.S. Provisional Patent Application No. 62/054,538 filed Sep. 24, 2014 the content of which is hereby incorporated herein.

FIELD

The present application relates to an apparatus, system and method for detecting evoked responses to a stimulus (a stimulus-response signal). In particular, the application relates to apparatus, system and method for detecting evoked responses when there is a low signal to noise ratio such as in electrophysiological evoked responses.

BACKGROUND

There are many situations in which it may be necessary to extract a signal of interest from a noisy received signal. This task becomes more difficult in a situation in which the received signal has a low signal to noise ratio (SNR). In some cases, the signal of interest may be generated in response to a stimulus and may also be synchronized to the stimulus. An example of such a case relates to the measurement of evoked responses. Electrophysiological evoked responses to a variety of stimuli are known to contain valuable clinical and scientific information in the assessment of the sensorineural systems of humans and animals. Evoked responses (ER), such as, for example, auditory evoked potentials, somatosensory evoked potentials, visual evoked potentials, otoacoustic emissions, or the like, are signals that are often 10-1000 times smaller than the noise that is typically recorded by signal transducers (such as electrodes or microphones) at the time of recording the ER. In many cases, the ER waveform and its clinically relevant features may only be detectable after averaging thousands of responses to individual stimuli.

The noise that is recorded by the signal transducers may be caused by various sources, including, for example, noise generated by muscular activity, for example, EMG noise, or the like, during an evoked response (ER) test and may also include electrical noise from lighting, other instruments and the like. Because the noise is generally many times greater than the ER signal, the noise tends to mask the ER signal. One challenge of clinical ER measurement is determining whether specific features of an ER waveform represent true electrophysiological responses or if the specific features are a result of noise. A special application of ER detection is the detection of the auditory brainstem response (ABR) and auditory steady state responses (ASSR) with applications to infant hearing screening and to the determination of auditory thresholds for all ages, which may be used in the customized fitting of hearing aids.

Several conventional techniques used to minimize noise in the recorded response to auditory stimuli are known. These techniques include, for example, signal averaging and weighted signal averaging, signal filtering, artifact rejection, and various techniques designed to relax or sedate the subject.

Signal averaging involves stimulating the patient with multiple stimuli, obtaining multiple time-based data series, each data series synchronized to a single instance of the stimulus, and averaging the multiple synchronized data series. Limitations of this traditional averaging method in evoked potential acquisition have long been recognized. A problem may arise from a poor signal to noise ratio (SNR) and that the number of averages required typically increases in inverse proportion to the square of the SNR.

Artifact rejection (AR) can be used to eliminate a data series or groups of data series that are most contaminated with noise, by excluding from the average those data series for which the noise exceeds a preset threshold.

Weighted averaging (WA) may further improve SNR by weighting groups of data series in inverse proportion to their noise content. There are various conventional methods of assessing noise content of a group of data series to determine the weights. Assuming the noise is quasi-stationary, i.e. stationary within each group of data series, and independent between data series, weighting each group in inverse proportion to the variance of the noise within the group will minimize the squared error of the weighted average.

In a conventional example, a group of 250 responses to stimuli that were stimulated at a rate of 30 Hz can be examined and averaged. In this case, the group is greater than 8 seconds in duration. The drawback of this technique is that noise in evoked potential measurements is, in general, not stationary over an 8 second duration, especially when the time series is contaminated with interference from the patient's EMG caused by muscle activity. A further drawback where multiple groups of measurements are being made is that electrical noise in the environment is, in general, not independent from group to group, especially when a significant component of that noise is periodic or quasi-periodic such as noise arising from powerline interference or from coherent cortical EEG during deep sleep, or the like. For example, coherent or quasi-coherent EEG noise in the alpha band is particularly large under anesthesia, making the detection of cortical evoked potentials that contain significant frequency content in the alpha band particularly difficult.

An improvement to an averaging scheme or weighted averaging scheme may include using normative data for the ABR signal and EEG to estimate the magnitude of the noise component of the variance in the data series which is comprised of both signal and additive noise. If the signal model based on normative data is accurate, this technique allows estimation of the noise from individual data series instead of groups of data series. For this technique to be valid, the stationarity assumption may only be required for the duration of a single data series or response, typically, less than 100 ms. However, normative data is generally based on stimulus type and stimulus level and, in at least some cases, the noise might not necessarily be stationary, even at such a small duration.

In a different conventional approach, weights may be chosen to be inversely related to a measure of dissimilarity between individual data series and the estimated average. In an example, the weights may be inversely proportional to the mean squared error between each individual data series and the averaged signal estimate.

Overall, similar to other conventional methods noted above, the weighted techniques operate under the assumption that the noise from data series to data series is independent, i.e. the noise between pair of data series has zero covariance. If this independence assumption is not valid, the resulting weights will not be optimal in the sense that the mean squared noise in the weighted average will not be minimized. In evoked response signals, the independence assumption is generally not valid because of environmental noise, when present, such as sinusoidal noise arising from power-line frequencies and their harmonics, which are generally not independent and non-stationary.

Embodiments of the apparatus, system and method described herein are intended to address at least one of the difficulties of conventional methods of detecting an evoked response signal.

SUMMARY

In a first aspect, the present disclosure provides a method for detection of an evoked response signal in noise, the method including: generating a plurality of stimuli; receiving a noisy signal related to an evoked response to the plurality of stimuli; divide the noisy signal into a plurality of responses to the plurality of stimuli; estimate a statistic matrix for the plurality of responses; shrink the statistic matrix; calculate weights based on an inverse of the shrunk statistic matrix; apply weights to the plurality of responses to construct a final response; and output the final response.

In a particular case, the shrinking the statistic matrix may include: calculate a correlation between combinations of responses; create a list of negatively correlated pairs; for each negatively correlated pair in the list: determine if one of the responses in the pair is in a shrinkage list, if so, remove the pair from the list of negatively correlated pairs, otherwise, add both responses of the pair to the shrinkage list; when the list of negatively correlated pairs is empty, set all non-diagonal elements of the statistic matrix corresponding to responses in the shrinkage list to 0 to provide a shrunk statistic matrix; and return the shrunk statistic matrix.

In another particular case, the method may further include decomposing each response into a plurality of sub-responses to create a plurality of sets of sub-responses and performing the: estimate a statistic matrix for the plurality of responses; shrink the statistic matrix; calculate weights based on an inverse of the shrunk statistic matrix; apply weights to the plurality of responses to construct a final response; for each of the plurality of sets of sub-responses.

In yet another particular case, the decomposing comprises: performing a multilevel discrete wavelet transform on individual responses in a loop for each scale of the multilevel discrete wavelet transform, selecting a scale of the multilevel discrete wavelet transform and, for the selected scale: set wavelet coefficients for non-selected scales to 0; and perform a multilevel inverse discrete wavelet transform to obtain a time domain sub-response for the selected scale; and return a plurality of sets of sub-responses, each set comprising sub-responses having the same scale.

In still yet another particular case, the statistic may be covariance and the statistic matrix may be a covariance matrix.

In another particular case, the statistic matrix may be an array having greater than two dimensions.

In yet another particular case, the statistic may be root mean square and the statistic matrix may be a root mean array having greater than two dimensions.

In still another particular case, the divide the noisy signal into a plurality of responses to the plurality of stimuli may be based on the plurality of responses being synchronized with the plurality of stimuli.

In another aspect, the disclosure provides for an apparatus for detection of an evoked response signal in noise, the apparatus having: an input device configured to receive data related to a plurality of stimuli and a noisy signal related to the evoked response signal to the plurality of stimuli; and a processor configured to: receive the noisy signal from the input device and divide the noisy signal into a plurality of responses to the plurality of stimuli; estimate a statistic matrix for the plurality of responses; shrink the statistic matrix; calculate weights based on an inverse of the shrunk statistic matrix; and apply weights to the plurality of responses to construct a final response representing the evoked response signal.

In a particular case, when shrinking the statistic matrix the processor may be further configured to: calculate a correlation between combinations of responses; create a list of negatively correlated pairs; for each negatively correlated pair in the list: determine if one of the responses in the pair is in a shrinkage list, if so, remove the pair from the list of negatively correlated pairs, otherwise, add both responses of the pair to the shrinkage list; when the list of negatively correlated pairs is empty, set all non-diagonal elements of the statistic matrix corresponding to responses in the shrinkage list to 0 to provide a shrunk statistic matrix; and return the shrunk statistic matrix.

In another particular case, the processor may be further configured to decompose each response into a plurality of sub-responses to create a plurality of sets of sub-responses and performing the: estimate a statistic matrix for the plurality of responses; shrink the statistic matrix; calculate weights based on an inverse of the shrunk statistic matrix; apply weights to the plurality of responses to construct a final response; for each of the plurality of sets of sub-responses.

In yet another particular case, the processor, when decomposing each response, may be further configure to: perform a multilevel discrete wavelet transform on individual responses in a loop for each scale of the multilevel discrete wavelet transform, selecting a scale of the multilevel discrete wavelet transform and, for the selected scale: set wavelet coefficient for non-selected scales to 0; and perform a multilevel inverse discrete wavelet transform to obtain a time domain sub-response for the selected scale; and return a plurality of sets of sub-responses, each set comprising sub-responses having the same scale.

In still yet another particular case, the statistic may be covariance and the statistic matrix may be a covariance matrix.

In a particular case, the statistic matrix may be an array having greater than two dimensions.

In another particular case, the statistic may be root mean square and the statistic matrix may be a root mean square an array having greater than two dimensions.

In still another particular case, the divide the noisy signal into a plurality of responses to the plurality of stimuli may be based on the plurality of responses being synchronized with the plurality of stimuli.

In still another aspect of the disclosure, there is provided a system for detection of an evoked response signal in noise, the system comprising: a stimulus generator configured to generate a plurality of stimuli; a plurality of sensors configured to receive a noisy signal including an evoked response signal to the plurality of stimuli; an input device configured to receive data related to the plurality of stimuli and the noisy signal; a processor configured to: receive the noisy signal from the input device and divide the noisy signal into a plurality of responses to the plurality of stimuli; estimate a statistic matrix for the plurality of responses; shrink the statistic matrix; calculate weights based on an inverse of the shrunk statistic matrix; and apply weights to the plurality of responses to construct a final response representing the evoked response signal; and an output device to output the final response received from the processor.

In a particular case, when shrinking the statistic matrix the processor may be further configured to: calculate a correlation between combinations of responses; create a list of negatively correlated pairs; for each negatively correlated pair in the list: determine if one of the responses in the pair is in a shrinkage list, if so, remove the pair from the list of negatively correlated pairs, otherwise, add both responses of the pair to the shrinkage list; when the list of negatively correlated pairs is empty, set all non-diagonal elements of the statistic matrix corresponding to responses in the shrinkage list to 0 to provide a shrunk statistic matrix; and return the shrunk statistic matrix.

In another particular case, the processor may be further configured to decompose each response into a plurality of sub-responses to create a plurality of sets of sub-responses and performing the: estimate a statistic matrix for the plurality of responses; shrink the statistic matrix; calculate weights based on an inverse of the shrunk statistic matrix; apply weights to the plurality of responses to construct a final response; for each of the plurality of sets of sub-responses.

In still another particular case, the processor, when decomposing each response, may be further configure to: perform a multilevel discrete wavelet transform on individual responses in a loop for each scale of the multilevel discrete wavelet transform, selecting a scale of the multilevel discrete wavelet transform and, for the selected scale: set wavelet coefficients for non-selected scales to 0; and perform a multilevel inverse discrete wavelet transform to obtain a time domain sub-response for the selected scale; and return a plurality of sets of sub-responses, each set comprising sub-responses having the same scale.

In still yet another case, the statistic may be covariance and the statistic matrix may be a covariance matrix.

In a particular case, the statistic matrix may be an array having greater than two dimensions.

In another particular case, the statistic may be root mean square and the statistic matrix may be a root mean square array having greater than two dimensions.

In still yet another particular case, the divide the noisy signal into a plurality of responses to the plurality of stimuli may be based on the plurality of responses being synchronized with the plurality of stimuli.

Other aspects and features of the present disclosure will become apparent to those ordinarily skilled in the art upon review of the following description of specific embodiments in conjunction with the accompanying figures.

BRIEF DESCRIPTION OF THE DRAWINGS

Embodiments of the present disclosure will now be described by way of example only, with reference to the attached Figures.

DETAILED DESCRIPTION

The present application relates to an apparatus, system and method for detecting an evoked response signal and, in particular, to an evoked response in a series of data that contains synchronized signals, for example as a signal generated in response to a stimulus (a stimulus-response signal). In particular, the application relates to apparatus, system and method for detecting a signal when there is a low signal to noise ratio such as in electrophysiological evoked responses, for example, visual, auditory, and sensory responses.

The method of detecting a signal is particularly suited to the use of auditory evoked responses where the background noise, such as EEG noise and power-line noise is very large and quasi-sinusoidal. Embodiments of the apparatus, system and method herein are intended to reduce the negatively correlated noise from the resultant average in an improved manner comparatively to conventional techniques, for example standard weighted averaging, and the like.

Figure 1:
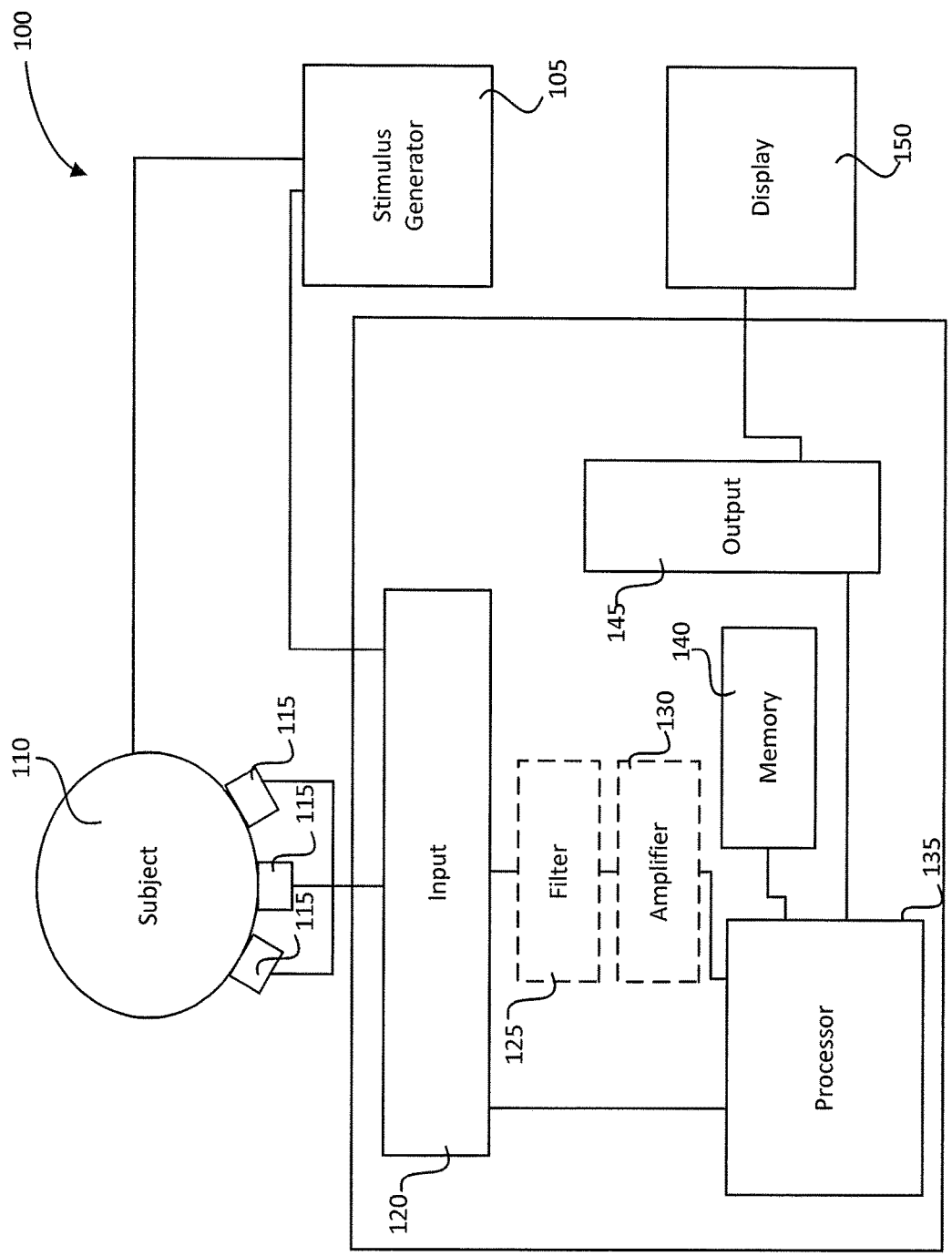
FIG. 1 illustrates an embodiment of an apparatus and system for evoked response detection.

An embodiment of an apparatus or system 100 for detection of an evoked response signal is shown in FIG. 1. The apparatus described herein is intended for electro-physiological signals such as advanced ABR or consciousness detection but a similar apparatus could be developed for other electro-physiological signals or applications by one of skill in the art on reviewing the description herein.

The system 100 includes a stimulus generator 105, which may be internal or external to other portions of the system and which provides a stimulus to a subject 110. A sensor or sensors 115, for example an electrode or electrodes, are provided to the subject to detect a noisy signal including a response to the stimulus, which is sent to an input module 120. The input module 120 may also receive input from the stimulus generator 105 related to the stimulus provided for synchronization purposes.

It will be understood that the electrodes receive continuous data, sometimes referred to as "noisy data" or "noisy signal". For each stimulus, a synchronized evoked response within the subject's brain will be generated. Typically, this evoked response will also be detected by the electrodes but is generally hidden in the noisy signal. Embodiments of the system, apparatus and method herein are intended to separate the evoked response, or stimulus-synchronized component, (sometimes referred to as a "response") from the non-synchronized components (i.e. noise). For ease of reference, a portion of the noisy signal that is expected to include a stimulus-synchronized component is also sometimes referred to as a "response" and is also referred to as a "sweep". In situations with poor signal to noise ratios (SNR), which are typical in physiological evoked responses, the detection of whether or not there is a response in the noisy signal generally involves providing a plurality of essentially identical stimuli and averaging a plurality of responses (i.e. portions of the noisy signal) corresponding to the stimuli. The final waveform or averaged response (sometimes called the "final response"), is the estimate of the synchronized evoked response, with reduced noise. It will be understood that the type of evoked response will generally be dependent on the stimulus and on the subject. For example, if a subject cannot hear an auditory stimulus, then there would not be an evoked response to the auditory stimulus.

Returning to FIG. 1, the input from the sensors 115 may be filtered, via a filter module 125, for example a bandpass filter or the like, before or after receipt at the input module 120 (In this example, the filter module 125 is shown after the input module but it may be helpful to provide filtering in advance of the input module). In some cases, the filter 125 may be attached to or incorporated into the sensor or sensors 115.

The system 100 may further include an amplifier 130. In some cases, the input from the input module 120 may be amplified prior to or after it has been filtered by the filter 125. In other cases, the amplifier 130 may be connected to or incorporated into the sensor or sensors 115.

The input module 120 provides data, for example data relating to the noisy signal and the stimuli, to a processor 135, which provides capability for various functions and/or modules as described below, while making use of a memory 140 for storing data, calculating results and the like. The processor 135 also provides capability for outputting data via an output module 145. In some cases, the processor 135 may also be connected with the stimulus generator 105 to provide instructions to the stimulus generator 105 and, in some cases, may also receive information directly from the stimulus generator 105. The output module 145 may output data in various formats as are known in the art, including, for example, output to a display 150 for review by a user of the system.

The stimulus generator 145 may include multiple stimulus sources, such as visual and auditory, or may be a single source. Further, in either case, the stimuli may generate a plurality of responses, such as an auditory stimulus that elicits both an ABR and an ASSR. Each response may or may not have a specific frequency band and filtering may be used in order to isolate each response-specific frequency band for analysis. As noted above, filtering may be before or after amplification and, further, each montage (i.e. electrode combination) may be provided with or subject to multiple filters.

Figure 2:
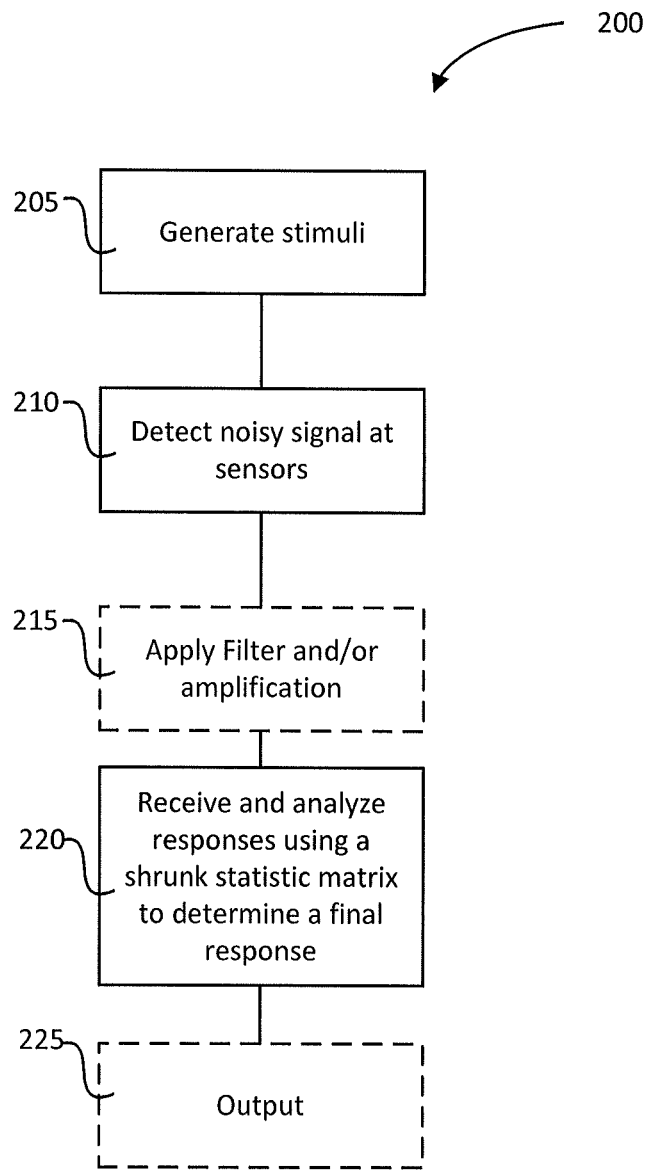
FIG. 2 illustrates an embodiment of a method for evoked response detection.

FIG. 2 illustrates an embodiment of a method 200 for detecting an evoked response signal generated in response to a stimulus. At 205, a plurality of stimuli is generated by the stimulus generator 105. At 210, a noisy signal containing a plurality of responses is detected by the sensor or sensors 115 and sent to the input module 120. In some cases, data from the generated stimuli or the noisy signal relating thereto may also be stored in memory 140.

At 215, in some cases filtering and/or amplification may be applied to the noisy signal, via, for example, filter 125 and amplifier 130. As noted above, the filtering and/or amplification may be performed either before or after the signal is received at the input module 120. In an example of filtering and considering an ABR stimulus, for example, between 30 and 3000 Hz, 100 and 1500 Hz, or other range depending on the stimulus rate, data outside that region of interest would be noise and the removal of that noise prior to subsequent signal processing may improve the analysis to determine the evoked response.

At 220, the noisy signal is analyzed by the processor 135 to separate individual responses, perform an analysis on the responses, and determine a final response, representing an estimated evoked response and indicative of whether or not an evoked response has been detected. At 225, the final response may be output via the output module 145 to, for example, the display 150. In some cases, the final response may also be saved to memory 140.

The following description provides further detail on embodiments of methods for analyzing the noisy signal to detect an evoked response.

As noted above, averaging and weighted averaging (WA) is sometimes used in analyzing a signal to improve SNR, for example, by weighting data series or groups of data series in inverse proportion to their noise content. However, in general, the weighted techniques operate under the assumption that the noise from data series to data series is independent, i.e. the noise between pairs of data series has zero covariance and, in most cases, this assumption may not be valid in evoked responses, depending on the environment.

Interestingly, the problem of optimal weighting of evoked responses can be seen as a variance minimization problem, that is attempting to determine a response such that the error variance in the response is minimized. Another way to consider this is that optimal weighting may be addressed by a method for deriving weights that result in an optimal weighted average, i.e. a weighted average with minimal variance (and hence minimal standard deviation).

The proposed method herein differs from conventional methods in, at least, that embodiments of the method make use of an estimate of a statistic, such as covariance, of the noise matrix rather than an estimate of the noise variance alone. Using this approach, global minimization of the noise variance in the average is intended to be achieved with weights that satisfy the equation:

$$w^* = \frac{\Sigma^{-1} 1}{1 \Sigma^{-1} 1} \quad \text{(equation 1)}$$

where $\Sigma^{-1}$ is an inverse of a matrix of a statistic related to the noise among measured response pairs and 1 is a vector of 1's. The following description deals with covariances between measured response pairs (and the matrix is referred to as the "covariance matrix"), however other statistics related to the noise may be substituted as appropriate. As discussed below, for example, another statistic could be an rms measure, and the matrix may be an array having greater than two dimensions. In the case of the covariance matrix, the covariance matrix can be predicted from, for example, the sample data used to predict variance data with clusters of data or the response data itself.

Other (non-global) solutions of the minimization problem can be developed when linear constraints are added. For example, finding a minimum variance for a given desired overall mean and the constraint that weights cannot be negative. Linear programming techniques can be used to derive a vector w that minimizes the noise variance $\sigma_N^2 = w^T \Sigma w$ with the linear constraints. These solutions can generally be expressed as a linear combination of the global minimum variance solution given above and the expected value of each individual input:

$$w^* = \Sigma^{-1}(\lambda_1 1 + \lambda_2 \mu) \quad \text{(equation 2)}$$

where $\mu$ is a vector of expected values of the individual results and coefficients $\lambda_i$ are derived using LaGrangian or numerical methods to minimize the variance.

Practical implementation of these minimization solutions, however, may be limited as the covariance matrix may not be known precisely. The estimated covariance matrix is generally based on a limited sample of data and generally may be considered to be ill conditioned. As a result, small errors in covariance estimation can lead to poor weight selections. Further, inversion of the matrix can amplify estimation errors. It is believed that, in evoked potential applications, the covariance matrix may be extrapolated from inter-stimulus data, for example, but keeping in mind that small inaccuracies in the covariance estimates may result in poor weighting choices. By nature, sampling may just be an estimation of the population.

In some cases, applying shrinkage to the covariance matrix can provide a more robust covariance matrix. In some cases, a shrinkage estimator may be provided that is a linear combination of the covariance predicted from sample data and a structured covariance, typically a constant covariance that is derived from the expected value of all the sample covariances. Other shrinkage techniques may be used that involve reducing the covariance to zero for most covariance pairs, leave the diagonal variance terms the same as the predicted variances, and using statistical techniques or the like that require the remaining covariance terms to exceed some threshold or be shrunk or set to zero.

The present disclosure provides an apparatus, system and method for applying shrinkage of the covariance matrix to evoked response applications and using the resulting modified covariance matrix to determine the weights for weighted averaging of the evoked potential response. Embodiments herein include estimating an initial covariance matrix. One of the methods described above or known in the art to estimate the covariance matrix from interstimulus, prestimulus or intrastimulus data may be used. Since errors in the covariance matrix may be amplified when the matrix is inverted, the covariance matrix is intended to be subjected to shrinkage as described herein. For example, in an embodiment, the diagonal elements of the covariance matrix may be untouched and represent the individual variances in each response. Some or all of the non-diagonal elements are then selectively shrunk toward the global expected covariance, which is typically zero.

Figure 3A:
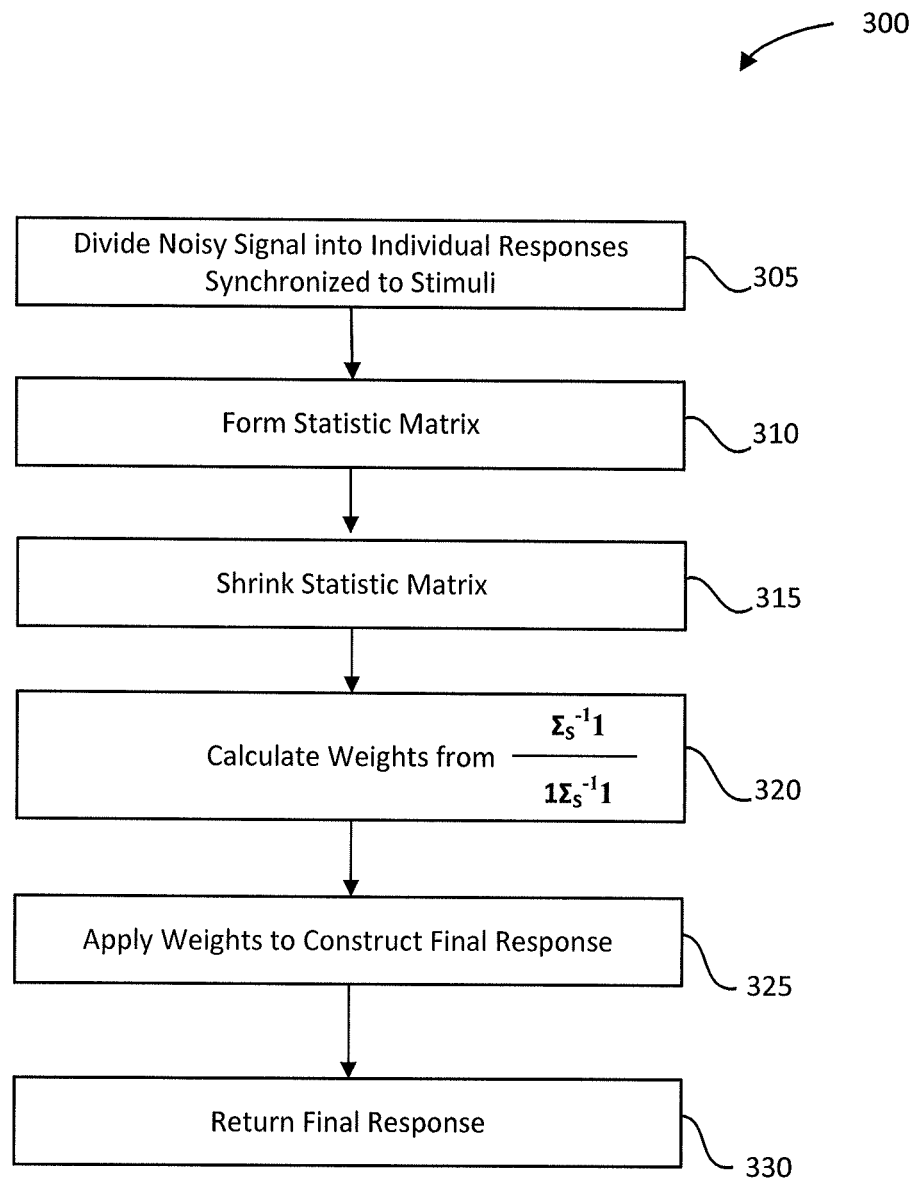
FIG. 3 illustrates an example of a method for detecting evoked responses using noise reduction with a covariance matrix.

FIG. 3A illustrates an embodiment of a method 300 for analyzing the noisy signal (220 in FIG. 2). At 305, the on-going EEG signal (noisy signal) is divided into a set of individual responses to the stimulus. In this particular embodiment, the division of individual responses is based on the responses being synchronized to the stimulus but one of skill in the art will understand that other ways of dividing the noisy signal may be available.

At 310, a matrix of a statistic related to the noise content is formed (in this embodiment, a covariance matrix) from the individual responses of 305. For the covariance example, for responses X and Y, the covariance may be calculated from, for example:

$$\operatorname{cov}(X, Y) = \frac{1}{n^2} \sum_{i=1}^{n} \sum_{j=1}^{n} \frac{1}{2}(x_i - x_j) \cdot (y_i - y_j)^T$$

At 315, the covariance matrix is shrunk. At 320, global minimum variance weights are calculated from the covariance matrix. At 325, weights are applied to the response data to construct a final response. At 330, a final response is returned.

Figure 4:
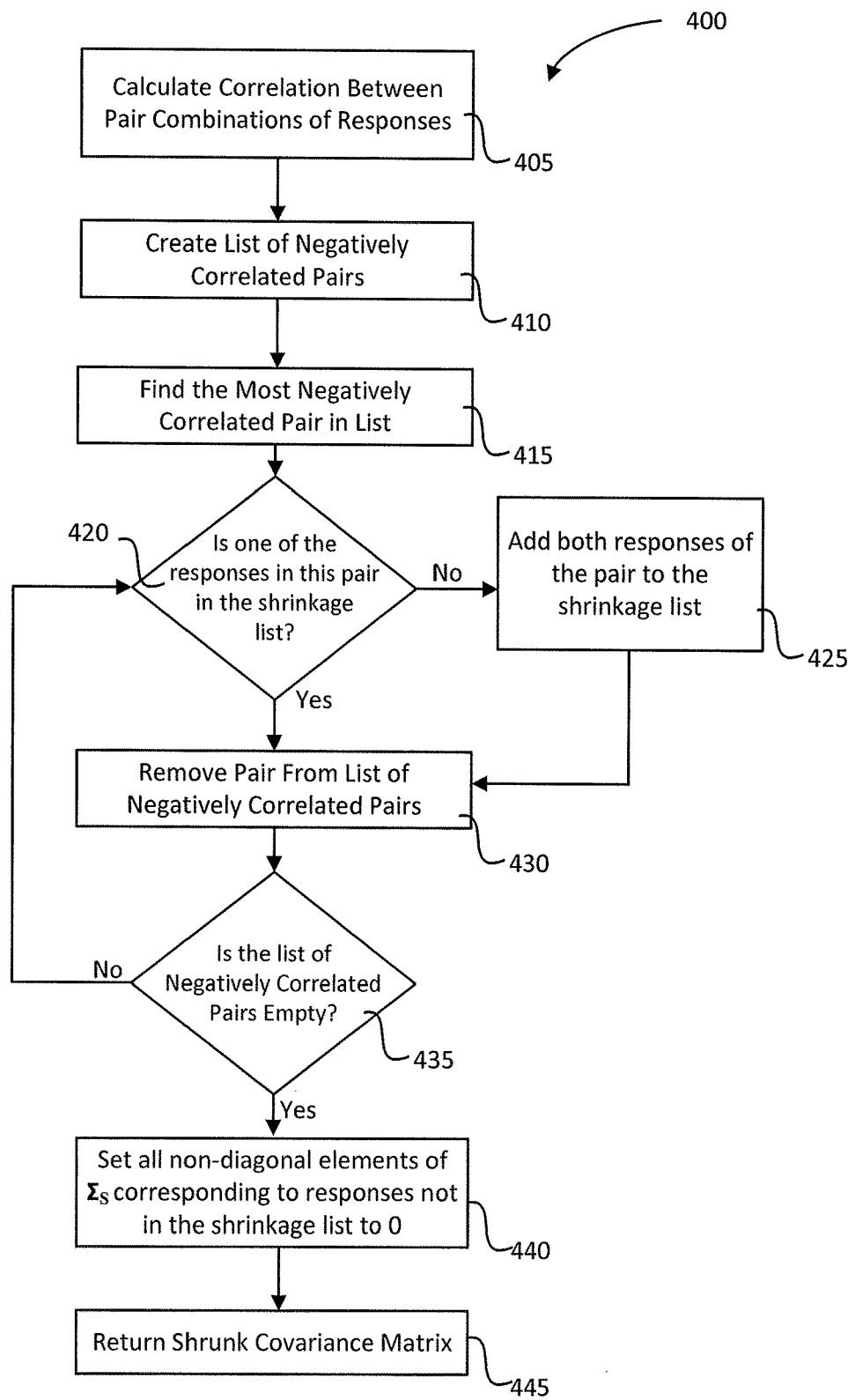
FIG. 4 illustrates an example of a method to shrink a covariance matrix.

The covariance matrix may be shrunk in one or more or a combination of manners. For example, in some cases, non-diagonal elements of the covariance matrix that are below some statistical threshold may be set to zero. In one example, the threshold may be set such that the covariance matrix becomes a sparse matrix. In another example, at most one non-zero non-diagonal element may be allowed for each response, resulting in at most one non-zero element in any non-diagonal row or column of the matrix. This constraint is intended to simplify the matrix inversion which can be reduced to a series of 2×2 matrix inversions. Further detail on one example of shrinking the covariance matrix is shown in FIG. 4.

Figure 3B:
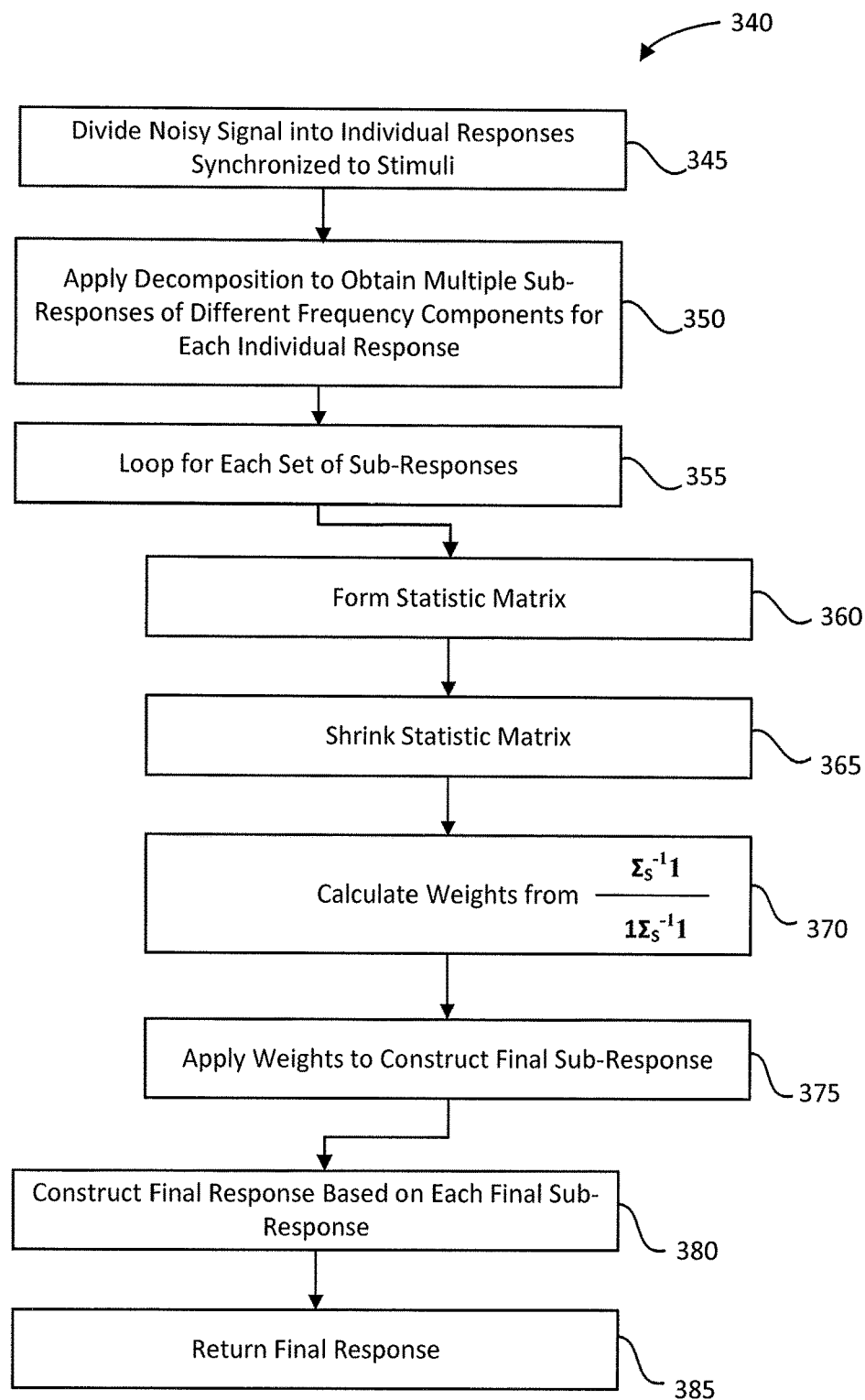

FIG. 3B illustrates another embodiment of a method 340 for analyzing the noisy signal (220 in FIG. 2). At 345, the on-going EEG signal (noisy signal) is divided into a set of individual responses to the stimulus. In this case, the division is based on the responses being synchronized to the stimuli.

At 350, a decomposition algorithm may be applied to obtain sub-responses, for example, of different frequency components, for each individual response. The sub-responses can then be arranged in sets made up of corresponding sub-responses from each response, for example, a set of sub-responses for each frequency component. An example method for obtaining the sub-responses using wavelets is described in further detail below with reference to FIG. 5. Other examples of decomposition methods include short-time Fourier transform, chirplets, and bandwidth (bank) filtering.

At 355, a loop for each set of sub-responses is performed in which a final sub-response is constructed. For each set of sub-responses, at 360, a covariance matrix is estimated. At 365, the covariance matrix is selectively shrunk. At 370, global minimum variance weights are calculated. At 375, weights are applied to construct a final sub-response. This process loops until all sub-responses have been processed.

At 380 the sub-responses are summed to produce a final response and, at 385, the final response is returned.

An embodiment of a method 400 for shrinking the covariance matrix is illustrated in FIG. 4. At 405, a correlation is calculated between pair combinations of responses. At 410, a list of negatively correlated pairs is created. At 415, the most negatively correlated pair is determined. At 420, it is determined whether one of the responses in the correlated pair is in a shrinkage list. If the response is not in the list, at 425, both responses of the pair are added to the shrinkage list. If the response is already in the list, or after it has been added to the shrinkage list, the pair is removed from the list of negatively correlated pairs, at 430. This preparation of the shrinkage list fulfils the criteria of at most one non-zero element in any non-diagonal row or column of the matrix.

At 435, it is determined whether there remain any negatively correlated pairs. If there are still pairs in the list, a loop is repeated until the list of negatively correlated pairs is empty. Once empty, at 440, all non-diagonal elements of the covariance matrix corresponding to responses not in the shrinkage list are set to 0. At 445, the shrunk covariance matrix $\Sigma_s$ is returned.

Another way of visualizing or considering the process of FIG. 4 is to make use of a correlation matrix containing correlation values for pairs of responses. For the correlation matrix, an upper-triangular correlation matrix is sufficient, since the lower triangular is just a reflection of the upper-triangular along the diagonal, which will be understood to be all "1's". First, all positively correlated pairs are set to zero. At this point, there are various approaches for selecting the pairs to remain while still maintaining the general criteria that no more than one non-diagonal element should be non-zero per row and column. As an example, with reference to the method of FIG. 4, next the most negatively correlated pair is selected and the remaining non-diagonal elements within the same row or column are set to zero. This is repeated with the next most negatively correlated pair of the remaining matrix and continued until there are no more negatively correlated pairs. This negative correlation matrix is then used as a "mask" such that, in the covariance matrix $\Sigma_s$, the elements corresponding to the zero elements in the negative correlation matrix are set to zero to provide a shrunk covariance matrix.

As a simple example, a method of creating a negative correlation matrix for six responses is as follows:

$$\begin{bmatrix} 1 & -0.8 & 0.3 & 0.1 & -0.9 & -0.6 \\ -0.8 & 1 & -0.2 & -0.7 & -0.8 & -0.4 \\ 0.3 & -0.2 & 1 & 0.5 & 0.4 & 0.9 \\ 0.1 & -0.7 & 0.5 & 1 & -0.1 & -0.5 \\ -0.9 & -0.8 & 0.4 & -0.1 & 1 & -0.7 \\ -0.6 & -0.4 & 0.9 & -0.5 & -0.7 & 1 \end{bmatrix}$$

Original Correlation Matrix $$\begin{bmatrix} 1 & -0.8 & 0.3 & 0.1 & -0.9 & -0.6 \\ 0 & 1 & -0.2 & -0.7 & -0.8 & -0.4 \\ 0 & 0 & 1 & 0.5 & 0.4 & 0.9 \\ 0 & 0 & 0 & 1 & -0.1 & -0.5 \\ 0 & 0 & 0 & 0 & 1 & -0.7 \\ 0 & 0 & 0 & 0 & 0 & 1 \end{bmatrix}$$

Setting Lower Triangular Components to Zero (Since Reflected)

$$\begin{bmatrix} 1 & -0.8 & 0 & 0 & -0.9 & -0.6 \\ 0 & 1 & -0.2 & -0.7 & -0.8 & -0.4 \\ 0 & 0 & 1 & 0 & 0 & 0 \\ 0 & 0 & 0 & 1 & -0.1 & -0.5 \\ 0 & 0 & 0 & 0 & 1 & -0.7 \\ 0 & 0 & 0 & 0 & 0 & 1 \end{bmatrix}$$

Removing Positive Correlations $$\begin{bmatrix} 1 & 0 & 0 & 0 & -0.9 & 0 \\ 0 & 1 & -0.2 & -0.7 & 0 & -0.4 \\ 0 & 0 & 1 & 0 & 0 & 0 \\ 0 & 0 & 0 & 1 & 0 & -0.5 \\ 0 & 0 & 0 & 0 & 1 & 0 \\ 0 & 0 & 0 & 0 & 0 & 1 \end{bmatrix}$$

Selecting most negative correlated element (1,5) and setting remaining non-diagonal elements in rows 1 and 5 and columns 1 and 5 to 0.

$$\begin{bmatrix} 1 & 0 & 0 & 0 & -0.9 & 0 \\ 0 & 1 & 0 & -0.7 & 0 & 0 \\ 0 & 0 & 1 & 0 & 0 & 0 \\ 0 & 0 & 0 & 1 & 0 & 0 \\ 0 & 0 & 0 & 0 & 1 & 0 \\ 0 & 0 & 0 & 0 & 0 & 1 \end{bmatrix}$$

Selecting the next most negative correlated element (2,4) and setting remaining non-diagonal elements in rows 2 and 4 and columns 2 and 4 to 0.

This correlation matrix is then used as a mask for the covariance matrix $\Sigma_s$ such that only pair 1,5 and 2,4 will be non-zero in the covariance matrix and thus used with regard to adjusting the weighting via the inverted covariance matrix.

In an alternative, it may be possible to extrapolate the negative correlation concept further by selecting a pairing combination that will give an optimized response, such as the sum of the correlation of the pairs that will give a maximum negative correlation. It will be noted that the criteria of no more than one non-diagonal element can be non-zero per row and column will generally be maintained in order to ease computation. A simple 4 response example is shown below:

$$\begin{bmatrix} 1 & -0.8 & -0.4 & 0.1 \\ -0.8 & 1 & -0.2 & -0.7 \\ -0.4 & -0.2 & 1 & 0.5 \\ 0.1 & -0.7 & 0.5 & 1 \end{bmatrix}$$

Original Correlation Matrix $$\begin{bmatrix} 1 & -0.8 & -0.4 & 0.1 \\ 0 & 1 & -0.2 & -0.7 \\ 0 & 0 & 1 & 0.5 \\ 0 & 0 & 0 & 1 \end{bmatrix}$$

Setting Lower Triangular Components to Zero (Since Reflected)

$$\begin{bmatrix} 1 & -0.8 & -0.4 & 0 \\ 0 & 1 & -0.2 & -0.7 \\ 0 & 0 & 1 & 0 \\ 0 & 0 & 0 & 1 \end{bmatrix}$$

Removing Positive Correlations
Option 1:

$$\begin{bmatrix} 1 & -0.8 & 0 & 0 \\ 0 & 1 & 0 & 0 \\ 0 & 0 & 1 & 0 \\ 0 & 0 & 0 & 1 \end{bmatrix}$$

Selecting negative correlated element (1,2) and setting remaining non-diagonal elements in rows 1 and 2 and columns 1 and 2 to 0. After doing this, there are no more remaining negative correlated pairs. Option 1 has a sum of −0.8.

Option 2:

$$\begin{bmatrix} 1 & 0 & -0.4 & 0 \\ 0 & 1 & 0 & -0.7 \\ 0 & 0 & 1 & 0 \\ 0 & 0 & 0 & 1 \end{bmatrix}$$

Selecting negative correlated element (1,3) and setting remaining non-diagonal elements in rows 1 and 3 and columns 1 and 3 to 0. After doing this, there is one more negative correlated pair at (2,4). Option 2 has a sum of −1.1

Option 3:

$$\begin{bmatrix} 1 & 0 & 0 & 0 \\ 0 & 1 & -0.2 & 0 \\ 0 & 0 & 1 & 0 \\ 0 & 0 & 0 & 1 \end{bmatrix}$$

Selecting negative correlated element (2,3) and setting remaining non-diagonal elements in rows 2 and 3 and columns 2 and 3 to 0. After doing this, there are no more remaining negative correlated pairs. Option 3 has a sum of −0.2.

Option 4:

$$\begin{bmatrix} 1 & 0 & -0.4 & 0 \\ 0 & 1 & 0 & -0.7 \\ 0 & 0 & 1 & 0 \\ 0 & 0 & 0 & 1 \end{bmatrix}$$

Selecting negative correlated element (2,4) and setting remaining non-diagonal elements in rows 2 and 4 and columns 2 and 4 to 0. After doing this, there is one more negative correlated pair at (1,3). Option 4 has a sum of −1.1. As such, the method would select the most negatively co-related result of Option 2 (which is the same as Option 4) instead of Option 1 or Option 3, and this Option 2 would be used to prepare the shrunk covariance matrix $\Sigma_s$. As can be seen from this simple example, this method may become more computationally extensive than the method of FIG. 4.

The method 400 may be used such that the correlation, corresponding to a covariance element/term, may be used to determine the threshold for inclusion of the covariance element/term in the shrunk covariance matrix such that only the most negatively correlated elements are included and all other elements are set to zero. Using negatively correlated elements only, combined with the constraint of one non-zero non-diagonal element per row or column, is intended to reduce computational complexity and ensure that the resulting weights are non-negative.

Following the shrinkage operation, weights may be chosen (320 and 370) to minimize the variance based on the shrunk/sparse covariance matrix. If the matrix is invertible, one example solution for global minimum variance weights is determined by equation 1:

$$w^* = \frac{\Sigma_s^{-1} 1}{1 \Sigma_s^{-1} 1}$$

where $\Sigma_s$ is the shrunk covariance matrix.

Alternatively the variance may be minimized with constraints on the w* vector such as limiting the value of a single weight below a predetermined threshold. In some applications, a priori knowledge of the signal may allow prediction. Minimization can also or alternatively be achieved using linear programming methods to choose a weighting vector w* that minimizes the equation $\sigma_N^2 = w^{*T} \Sigma_s w^*$ The technique of weighting evoked response measurements to reduce noise may be used in combination with other techniques, such as filtering and adaptive filtering. Filtering may be performed prior to or after completion of the method for detecting an evoked response.

As noted above at 350, another option for this technique is to decompose each individual response into multiple responses, for example, of different frequency components (in this case, the original response can be obtained from the sum of time domain reconstruction of each of these multiple responses).

Figure 5:
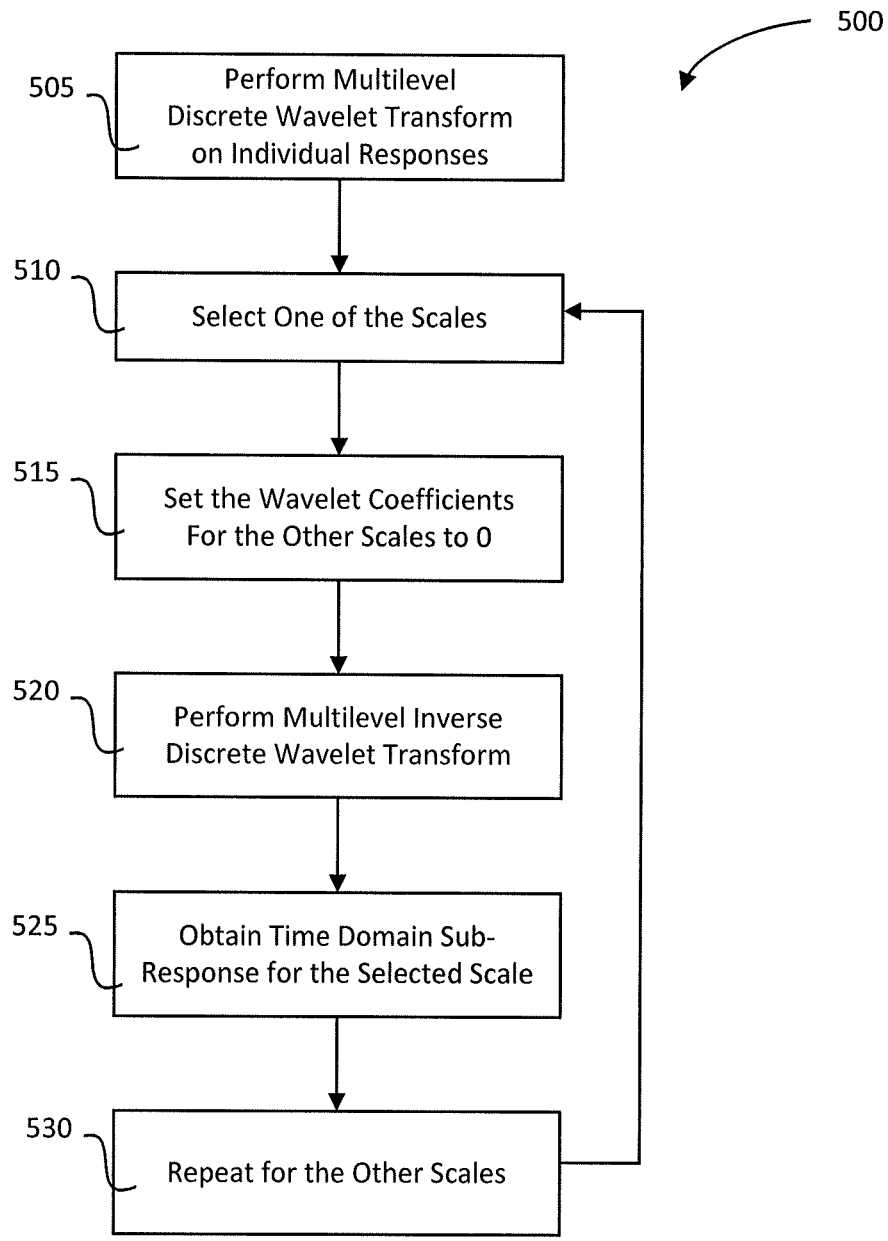
FIG. 5 illustrates an example of a method for the decomposition of a response into multiple sub-responses.

An embodiment of a method 500 of decomposition (350 from FIG. 3B) through wavelets is illustrated in FIG. 5. Each of a plurality of responses may be processed separately as per the above method for the whole response and the result may be a sum of the processed plurality of responses.

For example, at 505, a decomposition can be made through a discrete wavelet transform (DWT) as follows: each individual response is processed with a multilevel DWT to provide sub-responses in multiple scales or frequency bands in the wavelet domain. At 510, one of the plurality of sub-response scales is selected. At 515, a wavelet coefficient for each of the other scales is set to 0. At 520, a multi-level inverse discrete wavelet transformation is performed. At 525 a time domain sub-response is returned. This is repeated at 530 for the other scales (from 510 to 525).

As noted above, at 380 of FIG. 3B, the final response will simply be the sum of all the sub-responses from the plurality of wavelet scales (leveraging the mathematical properties of the wavelet transform).

The method 500 is intended to produce a time domain reconstruction for each scale, with each individual response equal to the sum of these time domain reconstructions. Each time domain reconstruction corresponding to a specific scale of the discrete wavelet transform is used to estimate a covariance matrix for that scale. Weights are estimated on a scale-by-scale basis as per the above procedure for the whole wave response and a final response is the sum of each scale's weighted response estimate. This enhancement of weighting of each scale takes advantage of the structure of the covariance matrix for each scale individually. This may be especially beneficial when the noise in the responses contains more than one sinusoidal component at different frequencies (that are separated into different wavelet scales) which would commonly occur when the noise is, for example, dominated by several power-line harmonics. This method of decomposition, may be applied to other synchronized signals, for example, other physiological signals.

Another option for the analysis of the responses (225 in FIG. 2) involves a multi-dimensional expansion (unlike the covariance matrix, which, is only two-dimensional), whereby another statistic, such as residual root mean square (rms), may be used instead of or in addition to covariance. This other statistic may be calculated based on the combination of measured response singles, pairs, triplets, quadruplets, and quintuplets (for example, a fifth-dimensional analysis). This multi-dimensional matrix or array will be the statistic matrix in 310 and 360 (in place of the covariance matrix from the description above). In the rms example, the diagonal of this matrix will be populated with the rms of the single responses and the three-dimensional matrix will be populated with the residual rms after combining each measured response pair, and each measured response triplet. Combining the response may be done as an average, weighted average, or other method. The shrinking may then be done with the constraint of only one non-zero non-diagonal element per dimension (row or column in two-dimension, as done above). For the example of rms, in the shrinking, the choice of which element(s) to include may be based, for example, on the element with the smallest residual rms in that dimension that is not in conflict with a smaller residual rms in an intersecting dimension using a process adapted from that of FIG. 4. In a similar way, the method of determining weights to be used, may be based on the statistic chosen. In the rms example, the weights may be calculated from the inverse of the residual rms of the shrunk matrix (with appropriate simplifications) as in 320 and 370, and the responses will be combined to construct the final response as in 325 and 375.

Experimental Results for Noise Reduction Techniques

To illustrate the effect of the detection methods herein in measuring the auditory brainstem response and in measuring the mismatched negativity (MMN) response, an embodiment of the apparatus, system and method described herein was implemented and its use in ABR and MMN examined. Sample results are presented herein. While results may vary somewhat from individual to individual and depending on the noise in each situation, it is believed that these results show the advantages of embodiments of the apparatus, system and method described herein.

ABR Experiment

Figure 6:
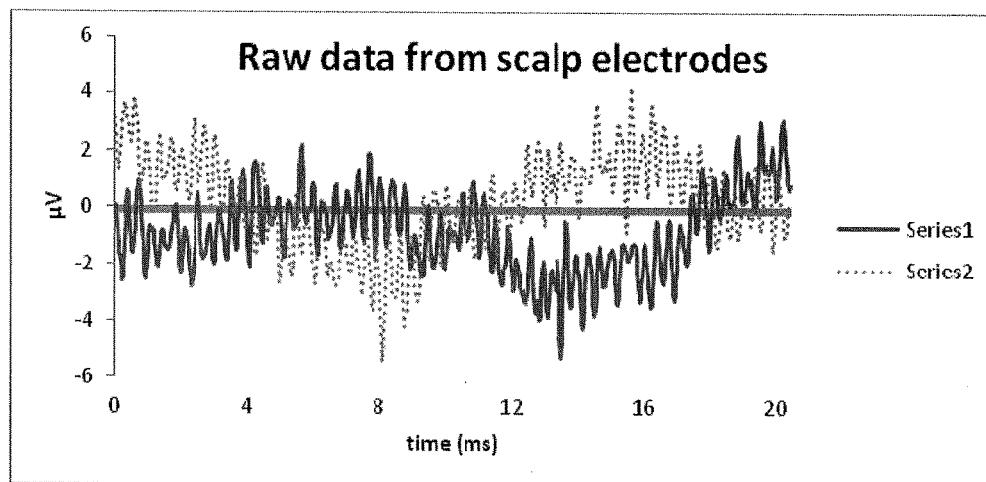
FIG. 6 illustrates sample data ("noisy signal") from electrodes in response to a stimulus.

In this experiment, responses were collected to auditory click stimuli (30 dB nHL) in the right ear of a newborn infant. The data was collected in a hospital environment that included several powerline harmonics from powered equipment. An example of raw data responses is shown in FIG. 6 and illustrates multiple powerline harmonics dominating the response. For 3200 responses, the variance and covariance of all response pairs was calculated and the data was used to populate the covariance matrix $\Sigma$. The covariance matrix was shrunk by leaving all the diagonal elements and applying all of the following three methods:

Method 1) create $\Sigma_s$ by setting all non-diagonal elements to zero. This method is similar to selecting weights for each response proportional to the inverse of the variance of the response. This is a conventional method.

Method 2)
a. Sort response pairs in order of the most negatively correlated first.
b. Select the most negatively correlated pairs in order, discarding pairs that include a response that has already been selected.
c. Create $\Sigma_s$ by leaving the value of the non-diagonal terms corresponding to the above selected pairs to their original value in $\Sigma$ and setting all other non-diagonal terms to zero.

Method 3)
a. Preprocess individual responses to an individual stimulus by applying a multilevel discrete wavelet transform (in this experiment a Biorthogonal 5.5 multilevel DWT), separating the response into 5 scales, which included 4 detail and 1 approximation.
b. Convert these scales back to the time domain by setting the wavelet coefficients for the other scales to zero and applying the corresponding multilevel inverse DWT.
c. Perform the following on a scale-by-scale basis for the time domain scale specific signals for all responses:
  i. Sort response pairs in order of the most negatively correlated first.
  ii. Select the most negatively correlated pairs in order discarding pairs that include a response that has already been selected.
  iii. Create $\Sigma_s$ by leaving the value of the non-diagonal terms corresponding to the above selected pairs to their original value in $\Sigma$ and setting all other non-diagonal terms to zero.

For all methods (for Method 3, this is performed on a scale-by-scale basis):
a. Calculate the minimum variance weights with the equation $$w^* = \frac{\sum_s^{-1} 1}{1 \sum_s^{-1} 1}$$

b. Calculate the weighted average of the responses using the above weighting vectors.
c. For Method 3 recombine the weighted average responses for all 5 scales by summing the weighted average calculated for each scale.

Figure 7:
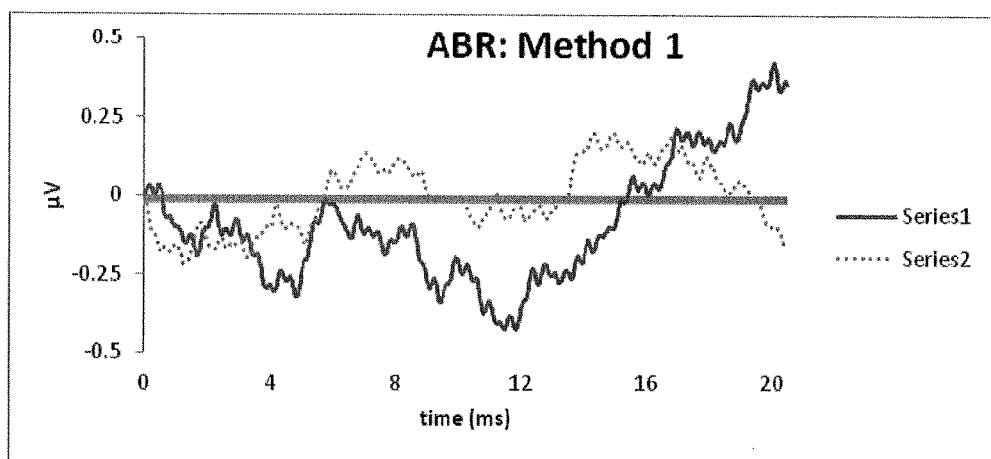
FIG. 7 illustrates a final response for an ABR experiment using Method 1.
Figure 8:
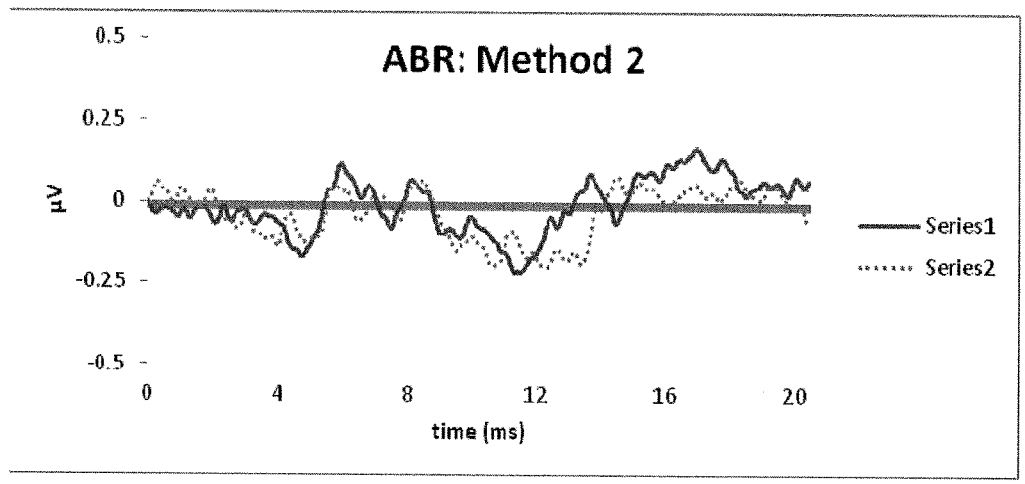
FIG. 8 illustrates a final response for an ABR experiment using Method 2.
Figure 9:
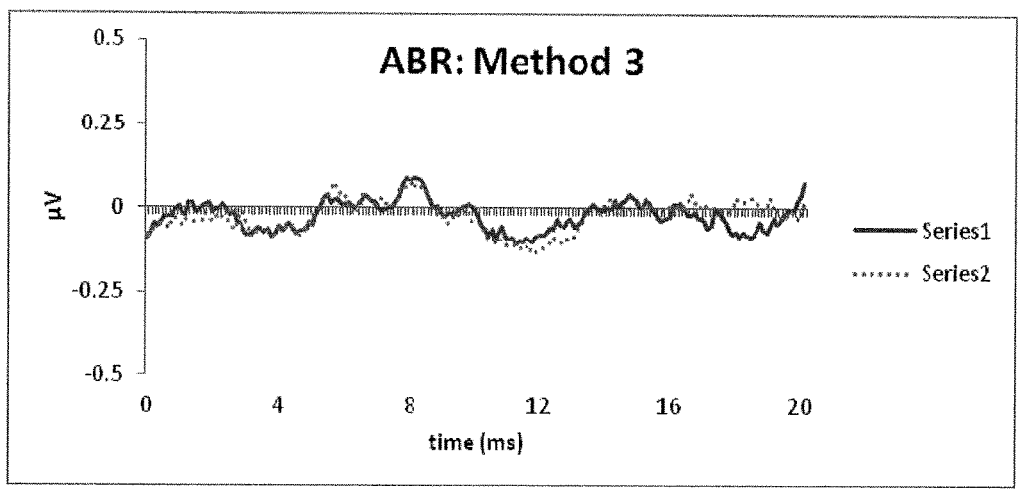
FIG. 9 illustrates a final response for an ABR experiment using Method 3.

Results of this experiment are illustrated in FIGS. 7, 8 and 9. In order to examine response repeatability for each method, the results are divided into 2 independent series. Half the data (1600 responses) were used to generate Series 1 and half the data (1600 responses) was used to generate Series 2. The division of the data into these groups/sets can be performed using various appropriate techniques, however, in this particular experiment, the technique used was the Monte Carlo procedure described in U.S. Pat. No. 8,484,270 to Kurtz.

It may be noted that, for all methods, the auditory brainstem response, known as Wave V, at about 8 milliseconds (peak followed by a negatively sloping wave) is clearly apparent. In FIG. 7, it is apparent that the response in Method 1 is impacted by 60 Hz power line noise, which may impact repeatability (as illustrated by differences between Series 1 and Series 2). Method 2 appears to reduce or eliminate the dominant 60 Hz harmonic but higher harmonics may negatively affect the repeatability of the response (the tracking of Series 1 and Series 2 is still not precise). Using Method 3, it is apparent that unwanted variance due to noise is minimized, as among these three methods.

Mismatch Negativity (MMN) Experiment

The mismatched negativity response is an evoked response that is generated to an odd or deviant stimulus in a sequence of otherwise similar stimuli. Although it is not dependent on attention, it is a cortical response and, as such, related to consciousness. The hypothesis of this experiment is that there is a detectable difference between the responses to standard and deviant stimuli when the patient is conscious but there is not a detectable difference during anesthesia and that the variability in the data will be reduced by making use of embodiments of the apparatus, system and method described herein.

A patient was stimulated with a short duration auditory chirp stimulus at an intensity of 65 dB HL at approximately 1.7 stimuli per second. Randomly inserted deviant stimuli that contained slightly higher frequency content than the standard stimuli were also applied. In the experiment, 426 responses to the standard stimulus and 107 responses to the randomly inserted deviant stimuli were collected from electrodes on the patient's scalp prior to the administration of anesthesia. This process was repeated during the maintenance phase of anesthesia. These responses were analyzed and weighted according to the three methods described in the ABR experiment described above and the performance was compared.

Figure 13:
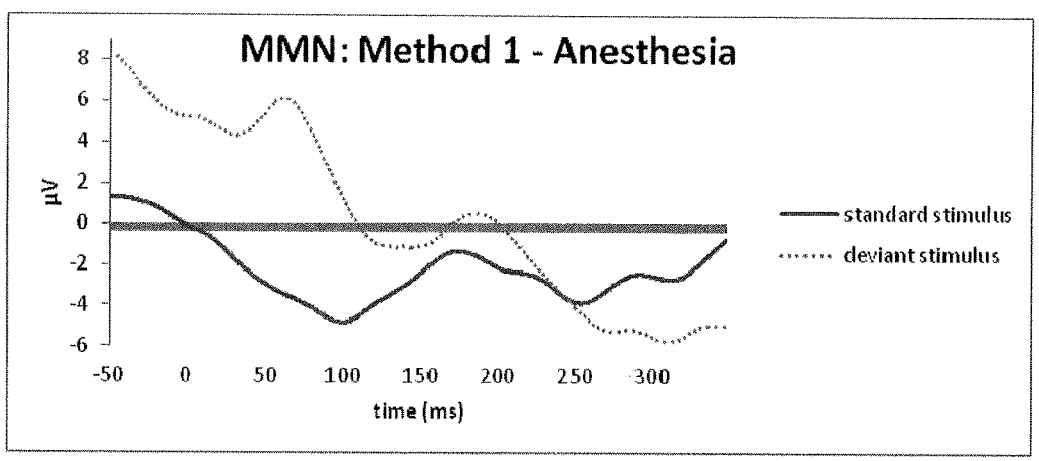
FIG. 13 illustrates a final response for an MMN experiment in a anesthetic condition using Method 1.
Figure 14:
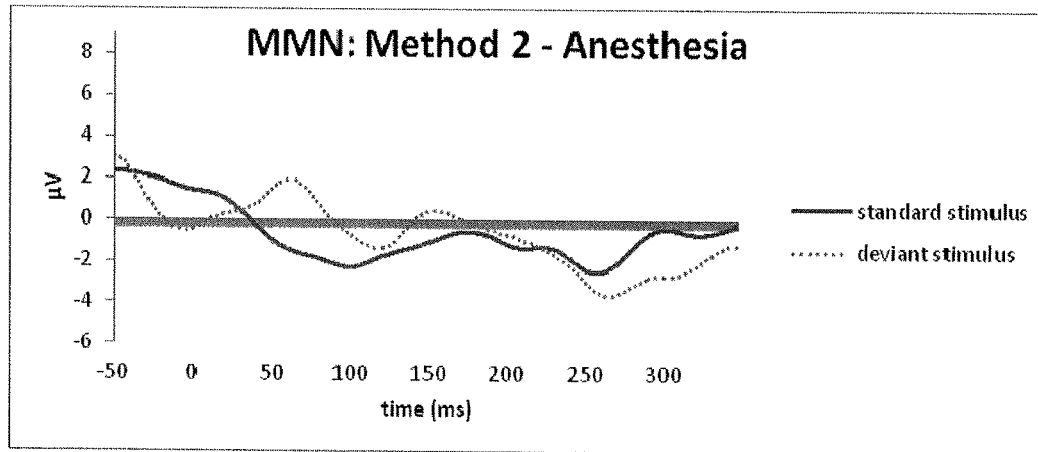
FIG. 14 illustrates a final response for an MMN experiment in a anesthetic condition using Method 2.
Figure 15:
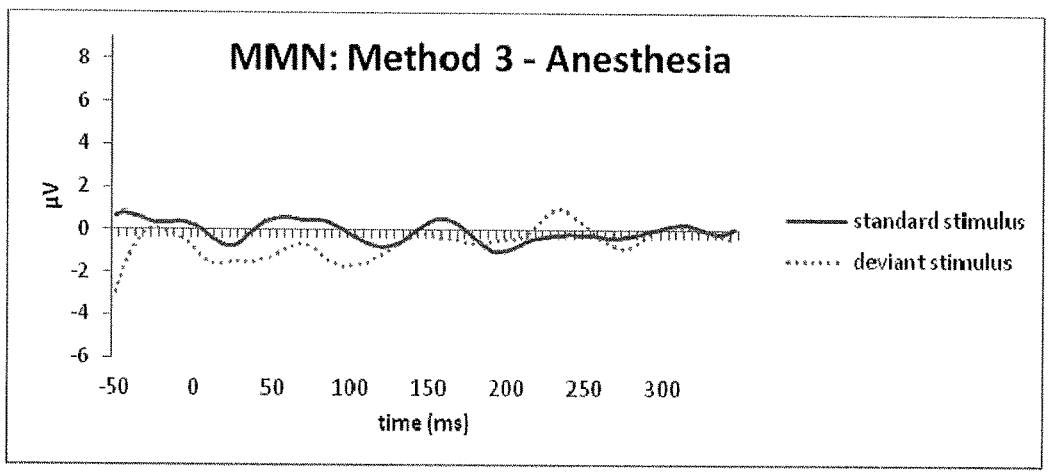
FIG. 15 illustrates a final response for an MMN experiment in a anesthetic condition using Method 3.

The results of the experiment using the 3 methods are displayed in the graphs in FIGS. 10, 11 and 12 for the pre-operative testing and FIGS. 13, 14 and 15 for the anesthesia testing and in Table 1 below. The MMN experiment is intended to illustrate the average standard and deviant responses as opposed to illustrating repeatability as in the ABR experiment described above. An MMN response is determined to be present when the peak amplitude of the processed deviant response is statistically different than that of a standard response in the region of expected MMN response (between 50 and 300 ms after onset of stimulus). As an MMN response depends on the consciousness state of the subject, in the awake pre-op state, we expect there to be a significant MMN, while in the anesthesia state, we do not expect there to be an MMN present.

Figure 10:
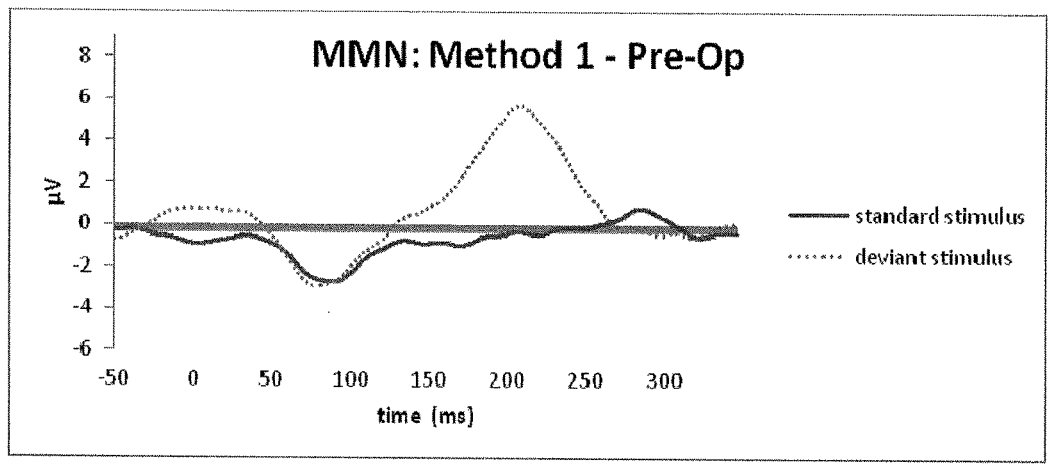
FIG. 10 illustrates a final response for an MMN experiment in a pre-operation condition using Method 1.
Figure 11:
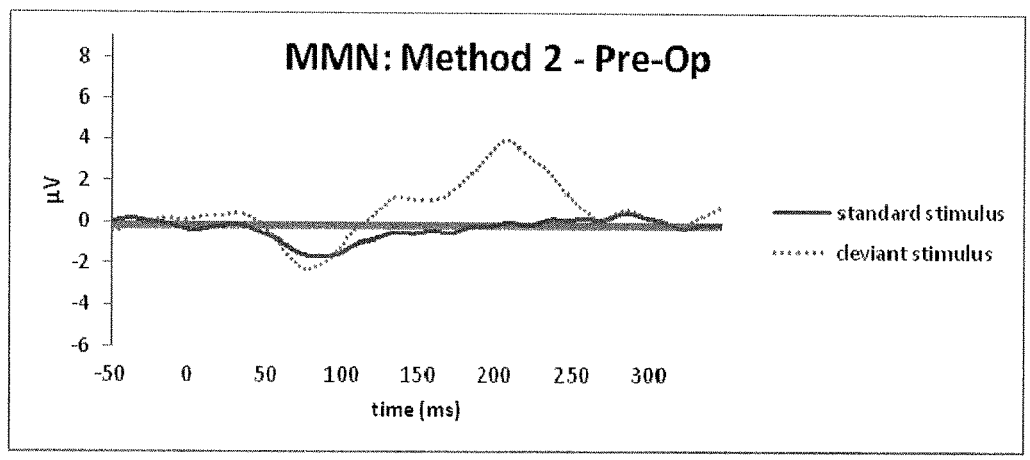
FIG. 11 illustrates a final response for an MMN experiment in a pre-operation condition using Method 2.

Using Method 1, a detectable response in the appropriate 50-300 ms time frame during the pre-operative period is clear (FIG. 10). There is also an artifactual response detected when the patient was unconscious under anesthesia (FIG. 13), which makes it difficult to determine if the patient is truly unconscious. This artifactual response is believed to be present because of the overwhelmingly large alpha band EEG present in the anesthesia condition. In particular, since the EEG noise is in the same frequency range as the signal, it interferes with the signal. The difference in peaks between the standard and deviant is high even in the anesthesia case. The statistically-based t-test in Table 1 illustrates that the response may not be statistically significant. The noise in this case would therefore appear to prevent definitive classification as to whether this patient is in the conscious state or not.

Using Method 2, however, the situation is significantly improved and the difference between the pre-operative data (FIG. 11) and the anesthesia data (FIG. 14) is clear. This example is believed to be generally typical of results using this method but there may be some variation based on, for example, the subject, the noise conditions and the like.

Figure 12:
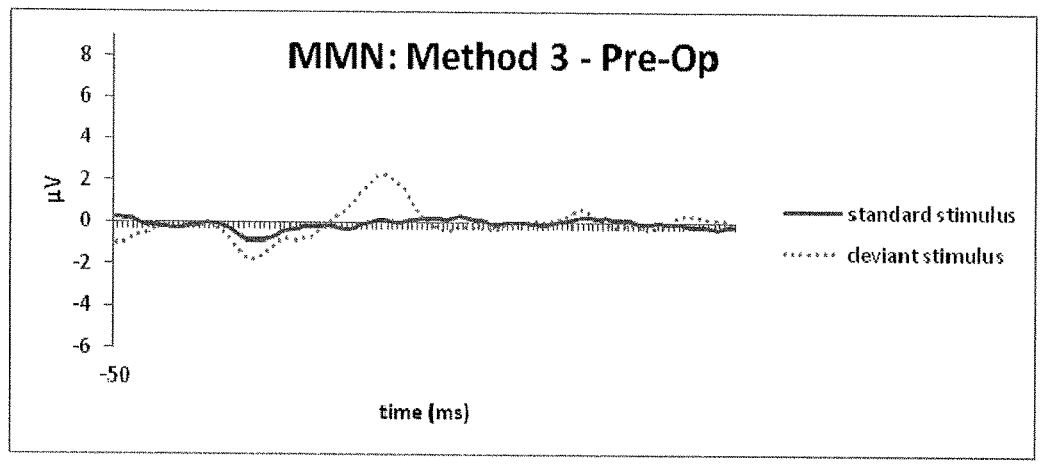
FIG. 12 illustrates a final response for an MMN experiment in a pre-operation condition using Method 3.

Using Method 3, the large alpha band was removed from the results, clearly showing the lack of an MMN response in the anesthesia data (FIG. 15) but maintaining a clear response in the pre-operative data (FIG. 12). Again, there may be some variation in the performance of the different methods based on, for example, the subject, the noise conditions and the like.

TABLE 1

MMN Performance: Comparing Peak Deviant with Peak Standard

|  | Difference ($\mu V$) | Standard Error | t-test |
|---|---|---|---|
| Pre-Op |  |  |  |
| Method 1 | 4.876 | 0.360 | 0.001 |
| Method 2 | 3.493 | 0.270 | 0.001 |
| Method 3 | 1.988 | 0.168 | 0.001 |
| Anesthesia |  |  |  |
| Method 1 | 2.515 | 2.083 | 0.314 |
| Method 2 | 0.846 | 0.920 | 0.426 |
| Method 3 | 0.289 | 0.292 | 0.396 |

In the preceding description, for purposes of explanation, numerous details are set forth in order to provide a thorough understanding of the embodiments. However, it will be apparent to one skilled in the art that these specific details may not be required. In other instances, well-known structures may be shown in block diagram form in order not to obscure the understanding. For example, specific details are not provided as to whether the embodiments or portions thereof described herein are implemented as a software routine, hardware circuit, firmware, or a combination thereof.

Embodiments of the disclosure or portions thereof can be represented as a computer program product stored in a machine-readable medium (also referred to as a computer-readable medium, a processor-readable medium, or a computer usable medium having a computer-readable program code embodied therein). The machine-readable medium can be any suitable tangible, non-transitory medium, including magnetic, optical, or electrical storage medium including a diskette, compact disk read only memory (CD-ROM), memory device (volatile or non-volatile), or similar storage mechanism. The machine-readable medium can contain various sets of instructions, code sequences, configuration information, or other data, which, when executed, cause a processor to perform steps in a method according to an embodiment of the disclosure. Those of ordinary skill in the art will appreciate that other instructions and operations necessary to implement the described implementations can also be stored on the machine-readable medium. The instructions stored on the machine-readable medium can be executed by a processor or other suitable processing device, and can interface with circuitry to perform the described tasks.

We claim:

1. A method for detection of an evoked response signal in noise, the method comprising:
   generating a plurality of stimuli;
   receiving a noisy signal related to an evoked response to the plurality of stimuli;
   dividing the noisy signal into a plurality of responses to the plurality of stimuli;
   calculating weights for the plurality of responses;
   identifying sets of responses, and for each set:
     combining the responses as a revised response;
     calculating a new weight for the revised response; and
     removing the responses from the plurality of responses;
   constructing a final response by weight averaging the revised responses and responses not identified in a set, the final response representing the evoked response or indicative of whether or not an evoked response has been detected; and
   outputting the final response.

2. The method of claim 1, further comprising:
decomposing each response into a plurality of sub-responses to create a plurality of sets of sub-responses, wherein each sub-response contains a particular subset of information from its corresponding response;
performing the steps of calculating, identifying, combining, calculating, removing and constructing for each of the plurality of sets of sub-responses; and
combining the final response of each set of sub-responses.

3. The method of claim 2, wherein each set of sub-responses corresponds to a particular frequency band.

4. The method of claim 3, wherein the particular frequency band is determined using wavelet decomposition.

5. The method of claim 1, wherein the step of dividing the noisy signal into a plurality of responses to the plurality of stimuli is based on the plurality of responses being synchronized with the plurality of stimuli.

6. The method of claim 1, wherein identifying sets of correlated responses comprises:
estimating a statistic matrix for the plurality of responses;
determining sets of correlated responses whose combination will result in noise reduction; and
shrinking the statistic matrix at least by removing or combining sets of correlated responses whose combination will result in noise reduction.

7. The method of claim 6, wherein shrinking the statistic matrix comprises:
creating a list of negatively correlated combinations of responses;
for each negatively correlated combination in the list:
determining if one of the responses in the combination is in a shrinkage list, and if so, removing the combination from the list of negatively correlated combinations, otherwise, add the responses of the combination to the shrinkage list;
when the list of negatively correlated combinations is empty, creating a mask for the statistic matrix;
applying the mask to the statistic matrix to provide a shrunk statistic matrix; and
returning the shrunk statistic matrix.

8. The method of claim 7, wherein one of:
the statistic is covariance and the statistic matrix is a covariance matrix of two dimensions; and
the statistic is root mean squared and the statistic matrix is a root mean squared matrix of two or more dimensions.

9. The method of claim 7, wherein the mask is created by:
creating a diagonal matrix of the same dimension as the statistic matrix; and
setting all non-diagonal elements of the statistic matrix corresponding to responses not in the shrinkage list to 0.

10. The method of claim 6, wherein the new weights are calculated based on an inverse of the shrunk statistic matrix.

11. The method of claim 6, wherein the sets of correlated responses are pair combinations of responses.

12. A non-transitory computer readable medium having stored thereon computer program code for execution by one or more processors to perform the method of claim 1.

13. An apparatus for detection of an evoked response signal in noise, the apparatus comprising:
an input device configured to receive data related to a plurality of stimuli and a noisy signal related to the evoked response signal to the plurality of stimuli; and
a processor configured to:
receive the noisy signal from the input device and divide the noisy signal into a plurality of responses to the plurality of stimuli;
calculate weights for the plurality of responses;
identify set of responses, and for each set:
combine the responses as a revised response;
calculate a new weight for the revised response; and
remove the responses from the plurality of responses;
construct a final response by weight averaging the revised responses and responses not identified in a set, the final response representing the evoked response or indicative of whether or not an evoked response has been detected; and
outputting the final response.

14. The apparatus of claim 13, wherein the processor is further configured to decompose each response into a plurality of sub-responses to create a plurality of sets of sub-responses, wherein each sub-response contains a particular subset of information from its corresponding response;
performing the steps of calculating, identifying, combining, calculating, removing and constructing for each of the plurality of sets of sub-responses; and
combining the final response of each set of sub-responses.

15. The apparatus of claim 13, wherein identifying sets of correlated responses comprises:
estimating a statistic matrix for the plurality of responses;
determining sets of correlated responses whose combination will result in noise reduction; and
shrinking the statistic matrix at least by removing or combining sets of correlated responses whose combination will result in noise reduction.

16. The apparatus for detection of claim 15, wherein when shrinking the statistic matrix the processor is further configured to:
create a list of negatively correlated combinations of responses;
for each negatively correlated combination in the list:
determine if one of the responses in the combination is in a shrinkage list, and if so, remove the combination from the list of negatively correlated combinations, otherwise, add the responses of the combination to the shrinkage list;
when the list of negatively correlated pairs combinations is empty, create a mask for the statistic matrix;
apply the mask to the statistic matrix to provide a shrunk statistic matrix; and
return the shrunk statistic matrix.

17. The apparatus of claim 16, wherein the processor is configured to create the mask by:
creating a diagonal matrix of the same dimension as the statistic matrix; and
setting all non-diagonal elements of the statistic matrix corresponding to responses not in the shrinkage list to 0.

18. The apparatus of claim 15, wherein the new weights are calculated based on an inverse of the shrunk statistic matrix.

19. The apparatus of claim 15, wherein the sets of correlated responses are pair combinations of responses.

20. A system for detection of an evoked response signal in noise, the system comprising:
a stimulus generator configured to generate a plurality of stimuli;

a plurality of sensors configured to receive a noisy signal including an evoked response signal to the plurality of stimuli;

an input device configured to receive data related to the plurality of stimuli and the noisy signal;

a processor configured to:
- receive the noisy signal from the input device and divide the noisy signal into a plurality of responses to the plurality of stimuli;
- calculate weights for the plurality of responses;
- identify set of responses, and for each set:
  - combine the responses as a revised response;
  - calculate a new weight for the revised response; and
  - remove the responses from the plurality of responses;
- construct a final response by weight averaging the revised responses and responses not identified in a set, the final response representing the evoked response or indicative of whether or not an evoked response has been detected; and an output device to output the final response received from the processor.

21. The system of claim 20, wherein the processor is further configured to decompose each response into a plurality of sub-responses to create a plurality of sets of sub-responses, wherein each sub-response contains a particular subset of information from its corresponding response;
- performing the steps of calculating, identifying, combining, calculating, removing and constructing for each of the plurality of sets of sub-responses; and
- combining the final response of each set of sub-responses.

22. The system of claim 20, wherein identifying sets of correlated responses comprises:

estimating a statistic matrix for the plurality of responses;
determining sets of correlated responses whose combination will result in noise reduction; and
shrinking the statistic matrix at least by removing or combining sets of correlated responses whose combination will result in noise reduction.

23. The system of claim 22, wherein when shrinking the statistic matrix the processor is further configured to:
- create a list of negatively correlated combinations of responses;
- for each negatively correlated combination in the list:
  - determine if one of the responses in the combination is in a shrinkage list, and if so, remove the combination from the list of negatively correlated combinations, otherwise, add the responses of the combination to the shrinkage list;
- when the list of negatively correlated combinations is empty, create a mask for the statistic matrix;
- apply the mask to the statistic matrix to provide a shrunk statistic matrix; and
- return the shrunk statistic matrix.

24. The system of claim 23, wherein the processor is configured to create the mask by:
- creating a diagonal matrix of the same dimension as the statistic matrix; and
- setting all non-diagonal elements of the statistic matrix corresponding to responses not in the shrinkage list to 0.

25. The system of claim 22, wherein the new weights are calculated based on an inverse of the shrunk statistic matrix.

26. The system of claim 22, wherein the sets of correlated responses are pair combinations of responses.

* * * * *